United States Patent
Tanabe et al.

(10) Patent No.: US 11,521,168 B2
(45) Date of Patent: Dec. 6, 2022

(54) SYSTEM AND METHOD FOR IPS CELL BANK USING MEDIA

(71) Applicants: FANUC CORPORATION, Yamanashi (JP); I Peace, Inc., Los Altos, CA (US)

(72) Inventors: Koji Tanabe, Los Altos, CA (US); Kiyonori Inaba, Yamanashi (JP); Masaru Oda, Yamanashi (JP)

(73) Assignees: FANUC CORPORATION, Yamanashi (JP); I PEACE, INC., Los Altos, CA (US)

( * ) Notice: Subject to any disclaimer, the term of this patent is extended or adjusted under 35 U.S.C. 154(b) by 128 days.

(21) Appl. No.: 16/445,213

(22) Filed: Jun. 19, 2019

(65) Prior Publication Data

US 2019/0303851 A1    Oct. 3, 2019

Related U.S. Application Data

(63) Continuation of application No. 15/228,022, filed on Aug. 4, 2016, now Pat. No. 10,373,109.

(51) Int. Cl.
*G06Q 10/08* (2012.01)
*C12N 5/074* (2010.01)
(Continued)

(52) U.S. Cl.
CPC .......... *G06Q 10/087* (2013.01); *G16H 40/20* (2018.01); *C12N 5/0696* (2013.01); *G06Q 10/06* (2013.01);
(Continued)

(58) Field of Classification Search
CPC ....... G06Q 10/087; G16H 40/20; G06F 19/00
(Continued)

(56) References Cited

U.S. PATENT DOCUMENTS 5,022,236 A   6/1991   Knippscheer et al.
5,325,678 A   7/1994   Borah et al.
(Continued)

FOREIGN PATENT DOCUMENTS

CN   102174395 A   9/2011
CN   205794637 U   12/2016
(Continued)

*Primary Examiner* — Robert W Morgan
*Assistant Examiner* — Rachel F Durnin
(74) *Attorney, Agent, or Firm* — Hauptman Ham, LLP

(57) ABSTRACT

A first terminal determines a collection date of a somatic cell based on a desired collection date and a collectable date transmitted by a second medium; and outputs the collection date to a first medium. A second terminal outputs the collectable date to the second medium; and determines an acceptance date based on the collection date transmitted by the first medium and a production period of an iPS cell transmitted by a third medium. A third terminal determines the production period based on the collection date and a producible period, and determines a shipment date based on the production period and stockable location and period transmitted by a fourth medium; and outputs the production period to the third medium. A fourth terminal outputs the stockable location and period to the fourth medium; and determines stock location and period based on the production period and the stockable location and period.

8 Claims, 4 Drawing Sheets

(51) Int. Cl.
  *G06Q 30/06* (2012.01)
  *G06Q 50/22* (2018.01)
  *G06Q 10/06* (2012.01)
  *G16H 40/20* (2018.01)

(52) U.S. Cl.
  CPC ......... *G06Q 10/0832* (2013.01); *G06Q 30/06* (2013.01); *G06Q 50/22* (2013.01)

(58) Field of Classification Search
  USPC ....................................................... 705/2–3
  See application file for complete search history.

(56) References Cited

U.S. PATENT DOCUMENTS

| | | | |
|---|---|---|---|
| 5,985,653 A | 11/1999 | Armstrong et al. | |
| 6,226,997 B1 | 5/2001 | Vago | |
| 2005/0276792 A1* | 12/2005 | Kaminski | G16H 10/60 435/372 |
| 2008/0215364 A1* | 9/2008 | Brevnova | G16H 40/67 705/2 |
| 2010/0272694 A1 | 10/2010 | Yang et al. | |
| 2011/0054929 A1* | 3/2011 | Centeno | G06Q 30/08 705/2 |
| 2011/0207209 A1 | 8/2011 | Hammons et al. | |
| 2013/0275236 A1 | 10/2013 | Koke et al. | |
| 2013/0325492 A1* | 12/2013 | Dudzinski | G16H 10/40 705/2 |
| 2013/0345094 A1 | 12/2013 | Noggle et al. | |
| 2014/0278499 A1* | 9/2014 | Bowman | G06Q 30/0601 705/2 |
| 2015/0203297 A1 | 7/2015 | Manning et al. | |
| 2015/0204598 A1 | 7/2015 | Affleck et al. | |
| 2015/0356500 A1 | 12/2015 | Larson et al. | |
| 2016/0114326 A1 | 4/2016 | Schryver | |
| 2016/0222355 A1* | 8/2016 | Noggle | C12N 5/0696 |
| 2016/0328521 A1* | 11/2016 | Mickles | G16H 10/60 |
| 2017/0299248 A1 | 10/2017 | High et al. | |
| 2017/0337337 A1* | 11/2017 | Heckerman | G16H 40/20 |

FOREIGN PATENT DOCUMENTS

| | | |
|---|---|---|
| JP | 2002027983 A | 1/2002 |
| JP | 2003108660 A | 4/2003 |
| JP | 2004119 A | 1/2004 |
| JP | 2004290134 A | 10/2004 |
| JP | 2004290140 A | 10/2004 |
| JP | 2004290147 A | 10/2004 |
| JP | 2005-112499 A | 4/2005 |
| JP | 2005285142 A | 10/2005 |
| JP | 20064299 A | 1/2006 |
| JP | 2008123 A | 1/2008 |
| JP | 2008-283972 A | 11/2008 |
| JP | 2011013752 A | 1/2011 |
| JP | 2012-243324 A | 12/2012 |
| JP | 2015502747 A | 1/2015 |
| JP | 2015100309 A | 6/2015 |
| JP | 2015130805 A | 7/2015 |
| JP | 2015-202918 A | 11/2015 |
| JP | 2015222539 A | 12/2015 |
| WO | 2010026656 A1 | 3/2010 |

\* cited by examiner

FIG. 3

Table 101:

| ENTRY ID | ENTRY DATE | CUSTOMER ID | FIRST DESIRED COLLECTION DATE | SECOND DESIRED COLLECTION DATE | THIRD DESIRED COLLECTION DATE |
|---|---|---|---|---|---|
| 0001 | 2018/02/19 | 0102 | 2018/03/15 | 2018/03/16 | 2018/03/17 |
| 0002 | 2018/02/23 | 0023 | 2018/03/18 | 2018/03/19 | 2018/03/22 |
| 0003 | 2018/02/25 | 0085 | 2018/03/21 | 2018/03/22 | 2018/03/25 |
| ... | ... | ... | ... | ... | ... |

Table 102:

| ACCEPTANCE ID | COLLECTION INSTITUTION ID | COLLECTABLE DATE | ENTRY ID | BLOOD COLLECTION DATE | BLOOD ACCEPTANCE DATE |
|---|---|---|---|---|---|
| 0001 | 0001 | 2018/03/16 | 0001 | 2018/03/16 | 2018/03/17 |
| 0002 | 0002 | 2018/03/21 | 0003 | 2018/03/21 | 2018/03/22 |
| 0003 | 0003 | 2018/03/25 | ... | ... | ... |
| ... | ... | ... | ... | ... | ... |

Table 103:

| PRODUCTION ID | iPS CELL PRODUCIBLE PERIOD | ENTRY ID | iPS CELL PRODUCTION PERIOD | iPS CELL SHIPPING DATE |
|---|---|---|---|---|
| 0001 | 2018/03/16~2018/09/16 | 0001 | 2018/03/16~2018/09/16 | 2018/09/16 |
| 0002 | 2018/03/17~2018/09/17 | 0003 | 2018/03/17~2018/09/17 | CANCELED |
| ... | ... | ... | ... | ... |

Table 104:

| STOCK SITE ID | STOCKABLE LOCATION | STOCKABLE PERIOD | ENTRY ID | STOCK LOCATION | STOCK PERIOD |
|---|---|---|---|---|---|
| 0001 | TOKYO STOCK SITE | 2018/09/19~2068/09/19 | 0001 | TOKYO STOCK SITE | 2018/09/19~2068/09/19 |
| 0002 | TOKYO STOCK SITE | 2018/09/20~2068/09/20 | 0003 | TOKYO STOCK SITE | ... |
| ... | ... | ... | ... | ... | ... |

SYSTEM AND METHOD FOR IPS CELL BANK USING MEDIA

RELATED APPLICATION

The present application is a continuation of U.S. application Ser. No. 15/228,022, filed Aug. 4, 2016. The disclosure of the above listed application is hereby incorporated by reference herein in its entirety.

BACKGROUND OF THE INVENTION

1. Field of the Invention

The present invention relates to a system and a method for an iPS cell bank using media.

2. Description of the Related Art

In recent years, the iPS Cell Stock Project has progressed in regenerative medicine. In the iPS Cell Stock Project, blood is collected from healthy human leukocyte antigen (HLA) homozygous donors, and induced pluripotent stem cells (iPS cells) are generated and stocked in the Center for iPS Cell Research and Application, Kyoto University. In such a background, it is considered that business (system construction) in which regenerative medicine and clinical research are conducted using the stocked iPS cells is essential and urgently needed. In this respect, for example, literatures described below are known as the technologies of managing the inventory of medical supplies and the temperature of drugs.

Japanese Unexamined Patent Publication (Kokai) No. 2012-243324 describes the invention of a system for managing the inventory and order of expendable supplies (chemical samples and calibrators) used in a clinical analyzer for analyzing blood, tissue, and the like.

Japanese Unexamined Patent Publication (Kokai) No. 2005-112499 describes the invention of a management system for performing inventory management and ordering of expendable supplies (syringes, bandages, and rubbing alcohol) used in hospitals.

Japanese Unexamined Patent Publication (Kokai) No. 2015-202918 describes a system for performing temperature management of factories and repositories for commodities needing temperature management, such as foods and drugs, and for performing temperature management of the commodities during transporting the commodities.

SUMMARY OF THE INVENTION

The time, cost, and effort of production of iPS cells for clinical use are hurdles for practical use. This is because there is no management system capable of performing the unified management of enormous data related to production management, quality management, and the like based on regulations as described below.

There is concern that it is impossible to maintain and ensure the quality of iPS cells when appropriate management is not performed in a step of accepting somatic cells which are ingredients for producing the iPS cells, a step of producing the iPS cells, a step of stocking the iPS cells, and a step of transporting the iPS cells. Against the concern, it is preferable to perform analysis based on, for example, "Standard for Biological Ingredients" for ingredients used for producing regenerative medical products, "Ministerial Ordinance on Good Gene, Cellular and Tissue-based Products" (Ministerial Ordinance on GCTP) for production and quality management, Notifications from the Director of the Ministry of Health, Labour and Welfare "Guideline on Ensuring Quality and Safety of Drug Product, etc. Derived from Processing of Human (Autologous) iPS (-like) Cells" and "Guideline on Quality and Safety Assurance of Drug Product, etc. Derived from Human (Allogenic) iPS (-like) Cells", Q5A and Q5D agreed in the International Conference on Harmonisation (ICH) for generation of a cell bank and for a virus free test, and the like.

It is preferable to strictly evaluate the quality of generated iPS cells for clinical use. As a manner in the whole quality management of pharmaceutical products obtained by processing human iPS cells, and the like (including iPS cells which are ingredients), there is a regulation that the standard and testing method of iPS cells are set, and the evidence thereof is provided. For example, the following quality evaluation items are demanded.

It is demanded to match various severe quality test management items such as:
1) cell count and survival rate;
2) identification test;
3) test of purity of cells;
4) process-related impurities testing;
5) sterility testing and mycoplasma negative testing;
6) endotoxin testing;
7) viral test;
8) characteristic test associated with iPS cells;
   (i) having pluripotency of being capable of differentiating into various somatic cells; and
   (ii) observing no gene mutation inducing cancer after transplantation, as well as low risk of tumorigenicity due to contamination of undifferentiated cells.

Construction of a foundation for stably supplying iPS cells to customers while maintaining and ensuring the quality of iPS cells is a future problem.

It is preferable to construct a management system capable of accurately and bi-directionally searching massive amounts and a wide variety of various data such as the data (sexes, ages, medical histories, health conditions, genetic backgrounds, and the like) of donors themselves, the data of acceptance of somatic cells as ingredients for generating iPS cells, the results of quality tests for generated iPS cells, and additional production and stock states.

Thus, it is demanded to construct a system for stably supplying high-quality iPS cells to a customer under accurate quality management.

A first aspect of the present invention is to provide a system for an iPS cell bank including: a entry management terminal that receives a request to produce an iPS cell from a customer; an acceptance management terminal that manages acceptance of a somatic cell including a blood cell, a skin cell, or the like as an ingredient for producing the iPS cell (hereinafter referred to as "somatic cell"); a production process management terminal that manages a step of producing the iPS cell; and a stock management terminal that manages stock of the produced iPS cell, wherein the entry management terminal includes: a first storage unit; an entry unit that makes an entry of the production request from the customer, including a desired date of collection of the somatic cell, as well as customer identification information for identifying the customer; a first determination unit that determines a date of collection of the somatic cell based on the desired collection date included in the entered production request; a first output unit that outputs the determined date of collection of the somatic cell to a first medium; and a first storage processing unit that stores, in the first storage unit, the determined date of collection of the somatic cell in association with the entered customer identification information; wherein the acceptance management terminal includes: a second storage unit that stores a collectable date on which the somatic cell can be collected; a second output unit that outputs the stored collectable date to a second medium; a second determination unit that determines a date of acceptance of the somatic cell based on the date of collection of the somatic cell, transmitted by the first medium; and a second storage processing unit that stores the determined date of acceptance of the somatic cell in the second storage unit; wherein the production process management terminal includes: a third storage unit that stores a producible period during which the iPS cell can be produced; a third determination unit that determines a period of production of the iPS cell based on the date of collection of the somatic cell, transmitted by the first medium, and on the stored producible period, and that determines a date of shipment of the produced iPS cell based on the determined period of production of the iPS cell; a third output unit that outputs the determined period of production of the iPS cell to a third medium; and a third storage processing unit that stores the determined period of production of the iPS cell and the determined date of shipment of the iPS cell in the third storage unit; wherein the stock management terminal includes: a fourth storage unit that stores a stockable location and a stockable period where the produced iPS cell can be stocked; a fourth output unit that outputs the stored stockable location and the stored stockable period to a fourth medium; and a fourth determination unit that determines a stock location and a stock period for stocking the produced iPS cell based on the period of production of the iPS cell, transmitted by the third medium and on the stored stockable location and stockable period; wherein the first determination unit determines the date of collection of the somatic cell based on the desired collection date and on the collectable date transmitted by the second medium; wherein the second determination unit determines the date of acceptance of the somatic cell based on the date of collection of the somatic cell and on the production period transmitted by the third medium; and wherein the third determination unit determines the date of shipment of the iPS cell based on the period of production of the iPS cell and on the stockable location and the stockable period transmitted by the fourth medium.

A second aspect of the present invention is to provide the system for the iPS cell bank according to the first aspect, wherein the somatic cell is a blood cell.

A third aspect of the present invention is to provide the system for the iPS cell bank according to the first or second aspect, wherein the first to fourth media are paper media.

A fourth aspect of the present invention is to provide the system for the iPS cell bank according to any one of the first to third aspects, wherein the entry management terminal, the acceptance management terminal, the production process management terminal, and the stock management terminal are connected communicatably to each other; and wherein the first to fourth media are communication media.

A fifth aspect of the present invention is to provide a method executed in a system for an iPS cell bank including: an entry management terminal that receives a request to produce an iPS cell from a customer; an acceptance management terminal that manages acceptance of a somatic cell for producing the iPS cell; a production process management terminal that manages a step of producing the iPS cell; and a stock management terminal that manages stock of the produced iPS cell, the method executed in the entry management terminal includes: a step of making an entry of the production request from the customer, including a desired date of collection of the somatic cell, as well as customer identification information for identifying the customer; a step of determining a date of collection of the somatic cell based on the desired collection date included in the entered production request; a step of outputting the determined date of collection of the somatic cell to a first medium; and a step of storing, in the first storage unit, the determined date of collection of the somatic cell in association with the entered customer identification information; the method executed in the acceptance management terminal includes: a step of storing a collectable date on which the somatic cell can be collected; a step of outputting the stored collectable date to a second medium; a step of determining a date of acceptance of the somatic cell based on the date of collection of the somatic cell, transmitted by the first medium; and a step of storing the determined date of acceptance of the somatic cell in the second storage unit; the method executed in the production process management terminal includes: a step of storing a producible period during which the iPS cell can be produced; a step of determining a period of production of the iPS cell based on the date of collection of the somatic cell, transmitted by the first medium, and on the stored cell producible period, and of determining a date of shipment of the produced iPS cell based on the determined period of production of the iPS cell; a step of outputting the determined period of production of the iPS cell to a third medium; and a step of storing the determined period of production of the iPS cell and the determined date of shipment of the iPS cell in the third storage unit; the method executed in the stock management terminal includes: a step of storing a stockable location and a stockable period where the produced iPS cell can be stocked; a step of outputting the stored stockable location and the stored stockable period to a fourth medium; and a step of determining a stock location and a stock period for stocking the produced iPS cell based on the period of production of the iPS cell, transmitted by the third medium and on the stored stockable location and stockable period; wherein the step of determining the date of collection of the somatic cell includes a step of determining the date of collection of the somatic cell based on the desired collection date and on the collectable date transmitted by the second medium; wherein the step of determining the date of acceptance of the somatic cell includes a step of determining the date of acceptance of the somatic cell based on the date of collection of the somatic cell and on the production period transmitted by the third medium; and wherein the step of determining the date of shipment of the iPS cell includes a step of determining the date of shipment of the iPS cell based on the period of production of the iPS cell and on the stockable location and the stockable period transmitted by the fourth medium.

According to one aspect of the present invention, each step is managed in consideration of the quality of a somatic cell which is an ingredient and an iPS cell to be a product, and therefore, a high-quality iPS cell can be stably supplied to a customer.

BRIEF DESCRIPTION OF THE DRAWINGS

FIG. 3 is a schematic view representing the table structure of a database (DB) according to the embodiment.

DETAILED DESCRIPTION

Figure 1:
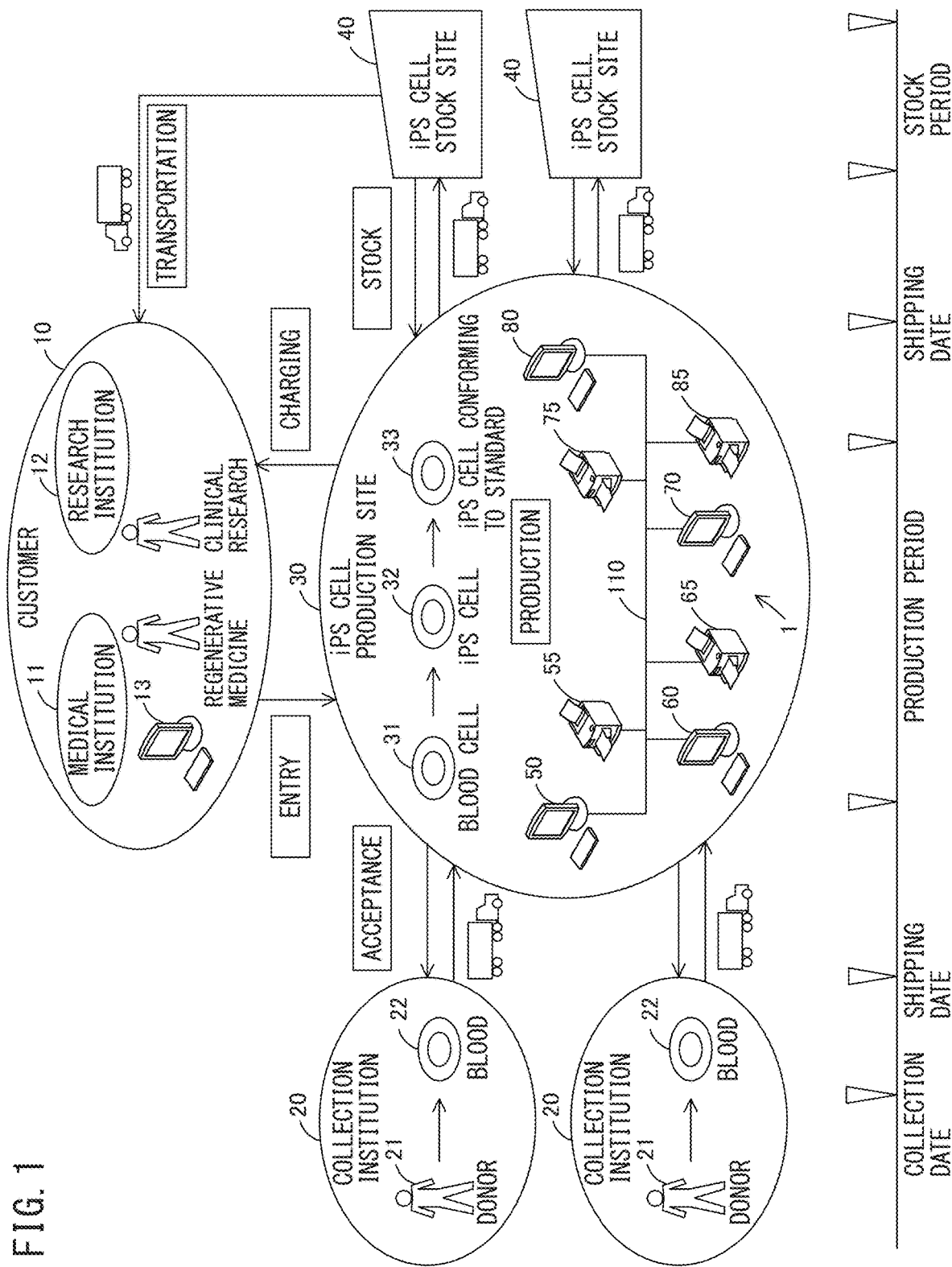
FIG. 1 is a schematic view illustrating a business model and a system for an iPS cell bank according to one embodiment of the present invention.

Embodiments of the present invention will be described in detail below with reference to the accompanying drawings. In each drawing, similar components are denoted by similar reference characters. The technical scope of the invention and the significance of terms described in Claims are not limited by contents described below.

(Summary of Business Model)

First, the summary of a business model according to the present invention will be described with reference to FIG. 1. FIG. 1 is a schematic view illustrating a business model and a system for an iPS cell bank according to an embodiment. The business model is a business model in which an iPS cell production site 30 receives a request to produce an iPS cell from a customer 10, accepts a somatic cell from a collection institution 20, generates an iPS cell 32 from the accepted blood, and evaluates the quality of the generated iPS cell 32, followed by stocking an iPS cell 33 conforming to a predetermined standard to an iPS cell stock site 40 and by transporting the iPS cell 33, by a transporting vehicle or aircraft, to the customer 10 depending on demand and charging the customer 10.

Examples of the customer 10 include a medical institution 11, a research institution 12, and other utilization institutions in which the iPS cell 33 is used. The customer 10 requests the iPS cell production site 30 to produce an iPS cell by telephone, facsimile, a customer terminal 13, or other request means. The customer 10 induces differentiation of the iPS cell provided in the business model to generate the cornea, the cardiac muscle, the liver, or another transplanted tissue cell, and uses the generated tissue cell in regenerative medicine, clinical research, or the like.

Examples of the collection institution 20 include a hospital, a blood donation site, and another collection institution in which a somatic cell 22 can be collected from a donor 21 such as a patient. Such collection institutions 20 are established in plural bases (for example, Tokyo, Osaka, Fukuoka, and the like). The collection institution 20 collects the somatic cell 22 from the donor 21 on a collection date of which notification is provided from the iPS cell production site 30, and ships the collected somatic cell 22 on a shipping date of which notification is provided from the iPS cell production site 30. The shipped somatic cell 22 is transported, by a transporting vehicle or aircraft, to the iPS cell production site 30 in the state of appropriately managing the temperature of the somatic cell.

Examples of the iPS cell production site 30 include a medical institution, a research institution, and another production institution in which the iPS cell 33 can be produced. The iPS cell production site 30 notifies the collection institution 20 of a collection date and an acceptance date automatically determined by a system 1 for an iPS cell bank to accept a somatic cell when receiving a production request from the customer 10. In such a manner, the collected blood is transported, by a transporting vehicle or aircraft, to the iPS cell production site 30.

The iPS cell production site 30 produces the iPS cell 33 within a production period automatically determined by the system 1 for the iPS cell bank. The iPS cell production site 30 introduces an inducer into a collected blood cell 31 which is a somatic cell to generate the iPS cell 32, and conducts a test of the quality of the generated iPS cell 32 (differentiation-inducing property testing, gene mutation testing, fungal, bacterial, and viral testing, and the like) to produce the iPS cell 33 conforming to the standard. The iPS cell production site 30 ships the iPS cell 33 to a stock location automatically determined by the system 1 for the iPS cell bank, on a shipping date automatically determined by the system 1 for the iPS cell bank. The shipped iPS cell 33 is transported, by a transporting vehicle or aircraft, to the iPS cell stock site 40 in the state of appropriately managing the temperature of the iPS cell 33.

Examples of the iPS cell stock site 40 include a warehouse, a medical institution, and another stock institution in which the iPS cell 33 can be stocked. Such iPS cell stock sites 40 are established in plural bases (for example, Tokyo, Osaka, Fukuoka, and the like). The iPS cell stock site 40 cryopreserves the iPS cell 33 and regularly conducts thawing testing during a stock period automatically determined by the system 1 for the iPS cell bank, as well as carries out reconfirmation when the iPS cell 33 is used. The iPS cell stock site 40 transports the stocked iPS cell 33 to the customer 10 depending on demand. The transported iPS cell 33 is transported, by a transporting vehicle or aircraft, to the customer 10 in the state of appropriately managing the temperature of the iPS cell 33.

(Configuration of System for iPS Cell Bank)

The configuration of the system for the iPS cell bank will now be described with reference to FIG. 1. The system 1 for the iPS cell bank manages an entry step of receiving a request to produce an iPS cell from a customer, an acceptance step of accepting the somatic cell 31, a production step of producing the iPS cell 33, a stock step of stocking the iPS cell 33, and a transportation step of transporting the iPS cell 33, by a transporting vehicle or aircraft, to the customer. The system 1 for the iPS cell bank includes terminal apparatuses 50 to 80 including first to fourth output units 55 to 85. The terminal apparatuses 50 to 80 are connected communicatably to each other through a network 110.

The terminal apparatuses 50 to 80 include a PC, a tablet PC, and another computer apparatus. The terminal apparatuses 50 to 80 include the entry management terminal 50 for managing the entry step, the acceptance management terminal 60 for managing the acceptance step, the production process management terminal 70 for managing the production step, and the stock management terminal 80 for managing the stock step. Each of the terminal apparatuses 50 to 80 has a DB in which the management information of each step is stored, and the DB has a relational database management system (RDBMS). The terminal apparatuses 50 to 80 are configured to output the management information of each step to the first to fourth output units 55 to 85.

Each of the first to fourth output units 55 to 85 includes a printer that outputs the management information of each step to a printing medium such as a paper medium or a film medium, or communication means that outputs the management information of each step to a communication medium such as a communication cable. The first to fourth output units 55 to 85 are configured to output the management information of each step to the printing medium or to the communication medium, thereby transmitting the management information to the other terminal apparatuses 50 to 80.

(Configuration of Terminal Apparatus)

Figure 2:
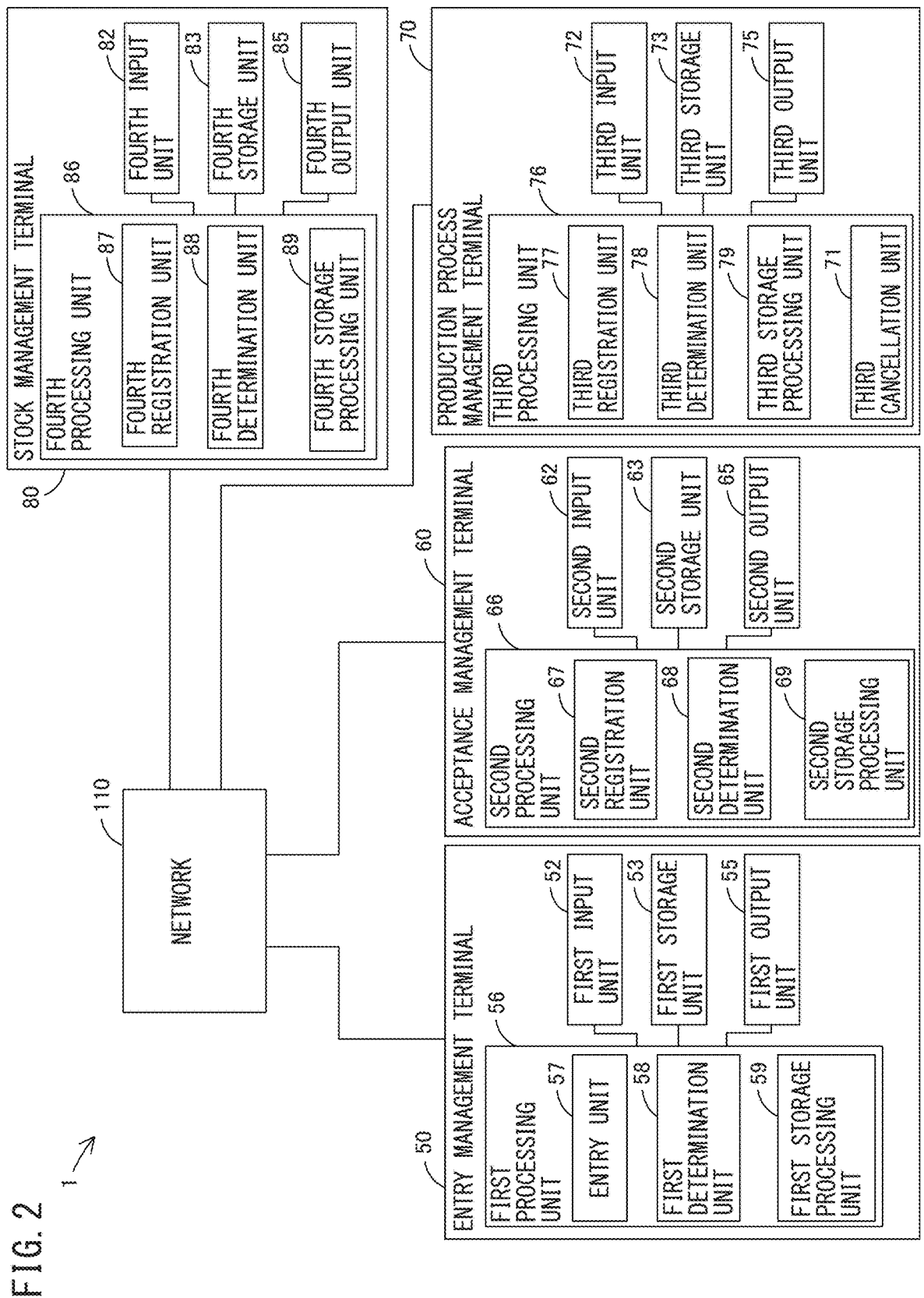
FIG. 2 is a block diagram illustrating terminal apparatuses according to the embodiment.

The configurations of the terminal apparatuses will now be described in more detail with reference to FIG. 2. FIG. 2 is a block diagram illustrating the terminal apparatuses according to the embodiment.

The entry management terminal 50 includes: a first input unit 52 including a keyboard, a mouse, a scanner, and other input means; a first storage unit 53 including a hard disk drive (HDD), a solid state drive (SSD), and other nonvolatile storage means; a first output unit 55 including a printer, communication means, and other output means; a first processing unit 56 including a central processing unit (CPU) and other processing means; an entry unit 57 including a user interface (UI) program; a first determination unit 58 including a business logic (BL) program; and a first storage processing unit 59 including a DB program.

The entry unit 57 provides an entry screen for making an entry of a production request from a customer, including a desired date of collection of blood as well as a desired location for stocking an iPS cell and a desired period of stock of the iPS cell as needed, as well as a customer ID for identifying the customer.

The first determination unit 58 determines a date of collection of a somatic cell based on the desired collection date included in the entered production request and on the collectable date transmitted by the second medium. When the second medium is a printing medium, the collectable date transmitted by the second medium is input by the scanner of the first input unit 52.

The first output unit 55 outputs the determined collection date to the first medium. When the first medium is a printing medium, the first medium is handed from a person responsible for entry to a production manager (a person responsible for entry makes a report to the production manager, and the production manager gives directions to a person responsible for a production process). When the first medium is a communication medium, the determined collection date is transmitted to the acceptance management terminal 60 and the production process management terminal 70 through the network 110.

The first storage processing unit 59 stores, in the first storage unit 53, the determined collection date in association with the entered customer ID.

The acceptance management terminal 60 includes: a second input unit 62 including a keyboard, a mouse, a scanner, and other input means; a second storage unit 63 including an HDD, an SSD, and other nonvolatile storage means; a second output unit 65 including a printer, communication means, and other output means; a second processing unit 66 including a CPU and other processing means; a second registration unit 67 including a UI program; a second determination unit 68 including a BL program; and a second storage processing unit 69 including a DB program.

The second registration unit 67 provides a registration screen for registering collectable dates on which somatic cells can be collected, which are obtained from plural collection institutions, as well as collection institution IDs for identifying the collection institutions.

The second storage processing unit 69 stores, in the second storage unit 63, the registered collectable dates in association with the collection institution IDs.

The second output unit 65 outputs the collectable dates to the second medium. When the second medium is a printing medium, the second medium is handed from a person responsible for acceptance to a person responsible for entry. When the second medium is a communication medium, the collectable dates are transmitted to the entry management terminal 50 through the network 110.

The second determination unit 68 determines a date of acceptance of the somatic cell based on the date of collection of the somatic cell, transmitted by the first medium, and on the production period transmitted by the third medium.

When the first medium or the third medium is a printing medium, the collection date transmitted by the first medium or the production period transmitted by the third medium is input by the scanner of the second input unit 62.

The second storage processing unit 69 stores, in the second storage unit 63, the determined date of acceptance of the somatic cell in association with the collection institution ID.

The production process management terminal 70 includes: a third input unit 72 including a keyboard, a mouse, a scanner, and other input means; a third storage unit 73 including an HDD, an SSD, and other nonvolatile storage means; a third output unit 75 including a printer, communication means, and other output means; a third processing unit 76 including a CPU and other processing means; a third registration unit 77 including a UI program; a third determination unit 78 including a BL program; a third storage processing unit 79 including a DB program; and a third cancellation unit 71 including a BL program.

The third registration unit 77 provides a registration screen for registering a producible period during which an iPS cell can be produced, and the quality test result of the iPS cell.

The third storage processing unit 79 stores the registered producible period in the third storage unit 73.

The third determination unit 78 determines a period of production of the iPS cell based on the date of collection of the somatic cell, transmitted by the first medium, and on the stored producible period. Further, the third determination unit 78 determines a date of shipment of the iPS cell based on the determined production period and on the stockable location and stockable period transmitted by the fourth medium. When the first medium or the fourth medium is a printing medium, the collection date transmitted by the first medium and the stockable location and stockable period transmitted by the fourth medium are input by the scanner of the third input unit 72.

The third output unit 75 outputs the determined production period to the third medium. When the third medium is a printing medium, the third medium is handed from the person responsible for a production process to the person responsible for acceptance and a person responsible for stock. When the third medium is a communication medium, the determined production period is transmitted to the acceptance management terminal 60 and the stock management terminal 80 through the network 110.

The third storage processing unit 79 stores the determined period of production of the iPS cell and the determined date of shipment of the iPS cell in the third storage unit 73.

The third cancellation unit 71 cancels the determined shipment of the iPS cell when the registered quality test result of the iPS cell is poor.

The stock management terminal 80 includes: a fourth input unit 82 including a keyboard, a mouse, a scanner, and other input means; a fourth storage unit 83 including an HDD, an SSD, and other nonvolatile storage means; a fourth output unit 85 including a printer, communication means, and other output means; a fourth processing unit 86 including a CPU and other processing means; and a fourth registration unit 87 including a UI program.

The fourth registration unit 87 provides a registration screen for registering stockable locations and stockable periods obtained from plural iPS cell stock sites, as well as stock site IDs for identifying the iPS cell stock sites.

A fourth storage processing unit 89 stores, in the fourth storage unit 83, the registered stockable locations and cell stockable periods in association with the stock site IDs.

The fourth output unit 85 outputs the stored stockable locations and stockable periods to the fourth medium. When the fourth medium is a printing medium, the fourth medium is handed from the person responsible for stock to the person responsible for a production process. When the fourth medium is a communication medium, the stockable locations and the stockable periods are transmitted to the production process management terminal 70 through the network 110.

The fourth determination unit 88 determines a stock location and a stock period for stocking the iPS cell based on the period of production of the iPS cell, transmitted by the third medium, and on the stored stockable locations and stockable periods where the iPS cell can be stocked. When the third medium is a printing medium, the production period transmitted by the third medium is input by the scanner of the fourth input unit 82.

The fourth storage processing unit 89 stores, in the fourth storage unit 83, the determined stock location and stock period in association with the stock site IDs.

(Table Structure of DB)

The table structure of a DB will now be described with reference to FIG. 3. FIG. 3 is a schematic view representing the table structure of the DB according to the embodiment. The request acceptance management terminal includes an entry table 101 in which a production request is stored, the acceptance management terminal includes an acceptance table 102 in which acceptance information is stored, the production process management terminal includes a production process table 103 in which production step information is stored, and the stock management terminal includes a stock table 104 in which stock information is stored.

The entry table 101 includes an entry ID, an entry date, a customer ID, and first, second, and third desired collection dates for a somatic cell.

The acceptance table 102 includes an acceptance ID, a collection institution ID, a collectable date on which a somatic cell can be collected, an entry ID, a date of collection of a somatic cell, and a date of collection of a somatic cell.

The production step table 103 includes a production ID, a producible period during which an iPS cell can be produced, an entry ID, a period of production of an iPS cell, and a date of shipment of an iPS cell.

The stock table 104 includes a stock ID, a stock site ID, a location where an iPS cell can be stocked, a stockable period during which an iPS cell can be stocked, an entry ID, a stock location of stocking an iPS cell, and a stock period of stocking an iPS cell.

(Operation of System for iPS Cell Bank)

Figure 4:
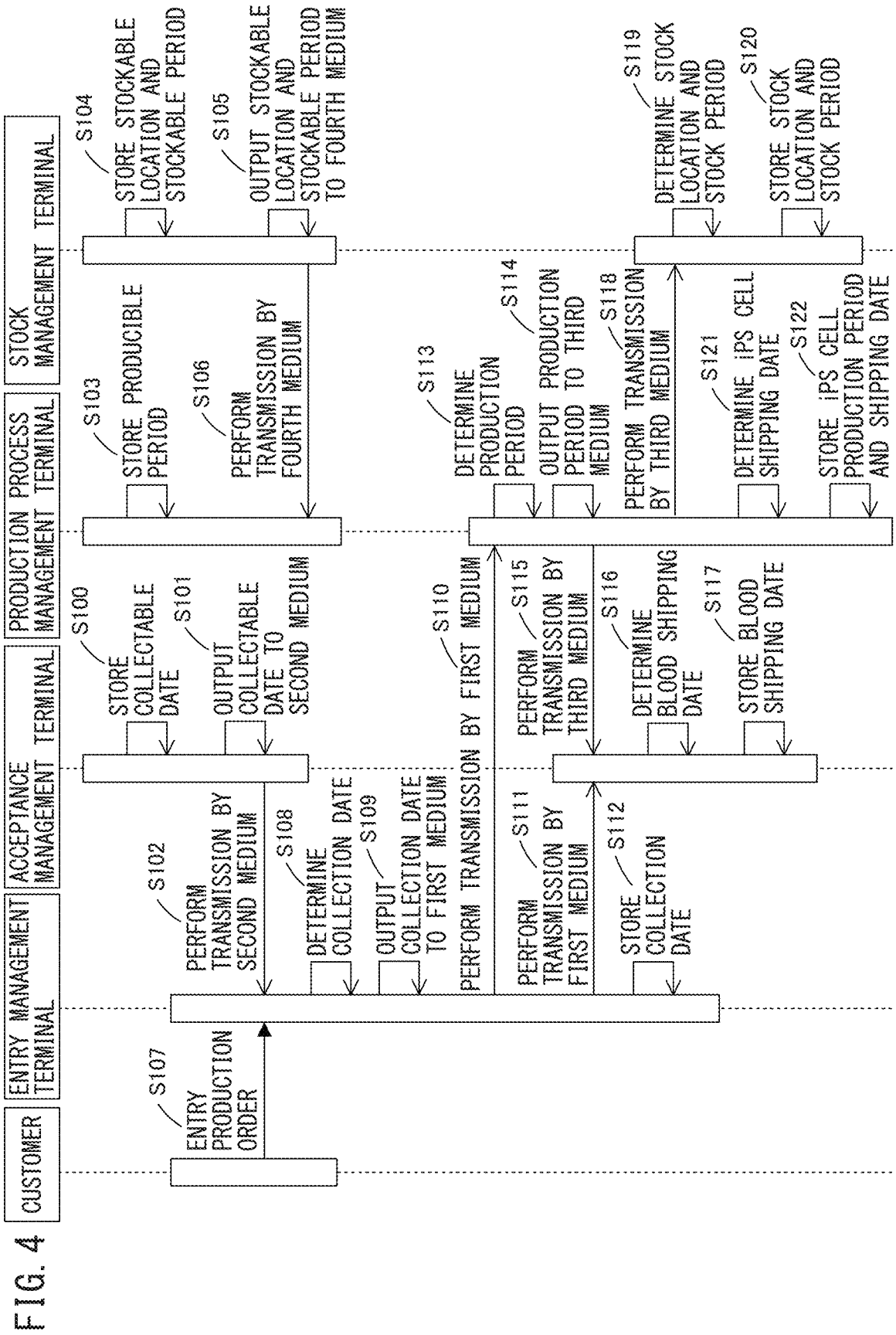
FIG. 4 is a sequence diagram representing the operation of the system for the iPS cell bank according to the embodiment.

The operation of the system for the iPS cell bank will now be described with reference to FIG. 4. FIG. 4 is a sequence diagram representing the operation of the system for the iPS cell bank according to the embodiment. Step S100 to step S107 may be carried out in any processing order.

In step S100, an acceptance management terminal stores, in the acceptance table, collectable dates obtained from plural collection institutions in association with collection institution IDs. Then, in step S101, the acceptance management terminal outputs the stored collectable dates to the second medium. In step S102, the collectable dates are transmitted to the entry management terminal by the second medium.

In step S103, a production process management terminal stores, in the production table, a producible period during which an iPS cell can be produced.

In step S104, a stock management terminal stores, in the stock table, stockable locations and stockable periods obtained from plural iPS cell stock sites in association with stock site IDs. Then, in step S105, the stock management terminal outputs the stored stockable locations and stockable periods to the fourth medium. In step S106, the stockable locations and the stockable periods are transmitted to the production process management terminal by the fourth medium.

In step S107, an entry management terminal receives a production request including first to third desired collection dates from a customer, as well as a customer ID. Then, in step S108, the entry management terminal determines a blood collection date based on the first to third desired collection dates included in the received production request and on the collectable dates transmitted by the second medium.

The processing of step S108 will now be described in detail with reference to FIG. 3. The entry management terminal extracts, from the collectable dates transmitted by the second medium, a collectable date of a collection institution matching the first desired collection date (2018/03/15) of a donor for an entry ID (0001). Because the collectable date matching the first desired collection date (2018/03/15) does not exist in the collectable dates transmitted by the second medium, the entry management terminal extracts, from the collectable dates transmitted by the second medium, a collectable date of a collection institution matching the second desired collection date (2018/03/16) of the donor. Because the collectable date (2018/03/16) matching the second desired collection date (2018/03/16) exists in the collectable dates transmitted by the second medium, the entry management terminal determines the collectable date (2018/03/16) as a collection date. When any collectable dates matching first to third desired collection dates do not exist in the collectable dates transmitted by the second medium, the entry management terminal provides notification of resetting of desired collection dates.

Referring to FIG. 4, subsequently, in step S109, the entry management terminal outputs the determined collection date to the first medium. In step S110, the collection date is transmitted to the production process management terminal by the first medium, and in step S111, the collection date is transmitted to the acceptance management terminal by the first medium. Then, in step S112, the entry management terminal stores, in the acceptance table, the determined collection date in association with the entered customer ID.

Then, in step S113, the production process management terminal determines a production period for producing an iPS cell based on the blood collection date transmitted by the first medium and on the stored producible period during which the iPS cell can be produced.

The processing of step S113 will be described in more detail with reference to FIG. 3. For the entry ID (0001), the production process management terminal adds a time of transportation of a somatic cell determined depending on a collection institution (for example, 1 day in the Tokyo collection site) to the collection date transmitted by the first medium (2018/03/16) to determine an earliest delivery date on which the somatic cell is delivered to the iPS cell production site earliest (2018/03/17), and adds a quality preservable period during which the quality of the collected somatic cell can be preserved (for example, 2 days in the case of blood) to determine a latest delivery date on which the somatic cell is delivered to an iPS cell production site latest (2018/03/18), whereby a cell deliverable period during which the somatic cell can be delivered from the collection institution to the iPS cell production site (2018/03/17 to 2018/03/18) is calculated. Then, the production process management terminal extracts, from the production process table 103, the earliest producible period (2018/03/16 to 2018/09/16) of producible periods (2018/03/16 to 2018/09/16, and 2018/03/17 to 2018/09/17) overlapping with the calculated deliverable period (2018/03/17 to 2018/03/18), and determines a production period during which an iPS cell is produced (2018/03/16 to 2018/09/16). As a result, a period of production of an iPS cell is determined in consideration of the quality of a somatic cell, and therefore, a high-quality iPS cell can be stably supplied to a customer. "Production period" in this example means a period from the acceptance of a somatic cell in an iPS cell production site to the completion of the evaluation of the quality of an iPS cell, and includes not only a substantial period of generation of the iPS cell (3 months) but also a period of evaluation of the quality of the generated iPS cell (3 months).

Referring to FIG. 4, in step S114, the production process management terminal then outputs the determined period of production of the iPS cell to the third medium. In step S115, the production period is transmitted to the acceptance management terminal by the third medium, and in step S118, the production period is transmitted to the stock management terminal by the third medium.

In step S116, subsequently, the acceptance management terminal determines an acceptance date on which the collected somatic cell is accepted in the iPS cell production site based on the date of collection of the somatic cell, transmitted by the first medium, and on the period of production of the iPS cell, transmitted by the third medium. In step S117, the acceptance management terminal then stores, in the acceptance table, the determined date of acceptance of the somatic cell in association with the collection institution ID.

The processing of step S116 will be described in more detail with reference to FIG. 3. For the entry ID (0001), the acceptance management terminal adds a time of transportation of the somatic cell (for example, 1 day in the Tokyo collection site) determined depending on a collection institution to the determined date of collection of the somatic cell (2018/03/16) to determine an acceptance date (2018/03/17), checks that the determined acceptance date (2018/03/17) is within the period of production of the iPS cell (2018/03/16 to 2018/09/16), and determines a date of acceptance of the somatic cell (2018/03/17).

Referring to FIG. 4, in step S119, the stock management terminal then determines a stock location and a stock period where the iPS cell is stocked based on the period of production of the iPS cell, transmitted by the third medium, and on the stored stockable locations and stockable periods. In step S120, the stock management terminal then stores, in the stock table, the determined stock location and stock period in association with the stock site ID.

The processing of step S119 will be described in more detail with reference to FIG. 3. For the request entry ID (0001), the stock management terminal adds a time of transportation of an iPS cell (for example, 1 day in the Tokyo stock site) determined depending on an iPS cell stock site to the date of the completion of the production period transmitted by the third medium (2018/09/16) to determine an earliest delivery date on which the iPS cell is delivered to the iPS cell stock site earliest (2018/09/17), and adds a quality assurance period during which the quality of the produced iPS cell can be ensured (for example, 4 days in the case of preservation in liquid nitrogen) to determine a latest delivery date on which the iPS cell is delivered to the iPS cell production site latest (2018/09/20), whereby a deliverable period during which the iPS cell can be delivered from the iPS cell production site to the iPS cell stock site (2018/09/17 to 2018/09/20) is calculated. Then, the stock management terminal extracts, from the stock table 104, a stockable period (2018/09/19 to 2068/09/19) which is the earliest stockable period (2018/09/19-2068/09/19) of stockable periods (2018/09/19 to 2068/09/19, and 2018/09/20 to 2068/09/20) overlapping with the calculated deliverable period (2018/09/17 to 2018/09/20), and determines a stock period (2018/09/19-2068/09/19) and a stock location (for example, Tokyo stock site) where an iPS cell is stocked. As a result, a stock location and a stock period are determined in consideration of the quality of an iPS cell, and therefore, a high-quality iPS cell can be stably supplied to a customer.

Referring to FIG. 4, in step S121, the production process management terminal then determines a date of shipment of the produced iPS cell based on the determined period of production of the iPS cell and on the stock location and stock period transmitted by fourth medium. In step S122, the production process management terminal then stores the determined period of production of the iPS cell and the determined date of shipment of the iPS cell in the production table.

The processing of step S121 will be described in detail with reference to FIG. 3. For the entry ID (0001), the production process management terminal adds a time of transportation of an iPS cell (for example, 1 day in the Tokyo stock site) determined depending on an iPS cell stock site to the date of the completion of the determined production period (2018/09/16) to determine an earliest delivery date on which the iPS cell is delivered to the iPS cell stock site earliest (2018/09/17), and adds a quality assurance period during which the quality of the produced iPS cell can be ensured (for example, 4 days in the case of preservation in liquid nitrogen) to determine a latest delivery date on which the iPS cell is delivered to the iPS cell production site latest (2018/09/20), whereby a deliverable period during which the iPS cell can be delivered from the iPS cell production site to the iPS cell stock site (2018/09/17 to 2018/09/20) is calculated. Then, the production process management terminal extracts, from the stockable periods transmitted by the fourth medium, a stockable period (2018/09/19 to 2068/09/19) which is the earliest stockable period (2018/09/19 to 2068/09/19) of stockable periods (2018/09/19 to 2068/09/19, and 2018/09/20 to 2068/09/20) overlapping with the calculated deliverable period (2018/09/17 to 2018/09/20), and determines a stock period (2018/09/19 to 2068/09/19) and a stock location (for example, Tokyo stock site). Subsequently, the production process management terminal subtracts a time of transportation of an iPS cell determined depending on an iPS cell stock site (for example, 1 day the Tokyo stock site) from the starting date (2018/09/19) of the determined stock period to determine a shipping date (2018/09/18), checks that the determined shipping date (2018/09/18) is after the date of the completion of the production period (2018/09/16), and determines a date of shipment of the iPS cell (2018/09/18).

Following step S122, the production process management terminal includes a step of registering the quality test result of the iPS cell, and a step of canceling the determined shipment of the iPS cell as represented in FIG. 3 when the registered quality test result of the iPS cell is poor.

The operation-effect of the system for the iPS cell bank of the embodiment will now be described. A high-quality iPS cell can be stably supplied to a customer because the production process management terminal determines a period of production of an iPS cell in consideration of the quality preservable period of a somatic cell (for example, 2 days in the case of blood) as described in the processing of step S113.

A high-quality iPS cell can be stably supplied to a customer because the stock management terminal determines a stock location and a stock period where an iPS cell is stocked in consideration of the quality assurance time (for example, 4 days in the case of preservation in liquid nitrogen) of an iPS cell conforming to a quality test as described in the processing of step S111.

All of the programs according to the embodiment are recorded on a computer-readable non-transitory recording medium, for example, CD-ROM, and thus provided.

The various embodiments have been described in the present specification. However, it should be understood that the present invention is not limited to the various embodiments described above, and various modifications can be made within the scope described in the following claims.

The invention claimed is:

1. A cell production management system for managing a production from a somatic cell to a target cell, the system comprising:
a first terminal apparatus, a second terminal apparatus, and a third terminal apparatus; and
a transporting apparatus that transports the somatic cell or the target cell,
wherein the first terminal apparatus comprises:
a first processor that
determines a collection date of the somatic cell based on (i) the desired date of collection of the somatic cell and (ii) a collectable date on which the somatic cell can be collected, and
controls outputting the determined collection date to a first medium,
wherein the second terminal apparatus comprises:
a second processor that
controls outputting the collectable date to a second medium, and
determines an acceptance date of the somatic cell based on (i) the collection date of the somatic cell, transmitted by the first medium, and (ii) a production period of the target cell,
wherein the third terminal apparatus comprises:
a third processor that
determines the production period of the target cell based on (i) the collection date of the somatic cell, transmitted by the first medium, and (ii) a producible period during which the target cell can be produced, and
controls outputting the determined production period of the target cell to a third medium, and
wherein the transporting apparatus transports the somatic cell collected on the collection date determined by the first processor so that the somatic cell is accepted on the acceptance date determined by the second processor.

2. The cell production management system according to claim 1,
wherein the third processor determines a shipping date of the target cell based on the production period, transmitted by the third medium, a stockable location and a stockable period,
wherein the transporting apparatus transports the target cell produced during the production period so that the target cell is shipped on the shipping date.

3. The cell production management system according to claim 2, further comprising:
a fourth terminal apparatus that is communicably connected to the first terminal apparatus, the second terminal apparatus, and the third terminal apparatus,
wherein the fourth terminal apparatus comprises a fourth processor that
controls outputting the stockable location and the stockable period to a fourth medium, and
determines a stock location and a stock period of the target cell based on the production period, transmitted by the third medium, and the stockable location and the stockable period, and
wherein the transporting apparatus transports the target cell stocked at the stock location during the stock period.

4. The cell production management system according to claim 3,
wherein the first terminal apparatus, the second terminal apparatus, the third terminal apparatus, and the fourth terminal apparatus are connected communicatably to each other, and
wherein the first to fourth media are communication media or paper media.

5. The cell production management system according to claim 1, wherein the third processor
adds a time of transportation of the somatic cell to the collection date of the somatic cell, transmitted by the first medium to determine an earliest delivery date on which the somatic cell is delivered to a cell production site earliest, and adds a quality preservable period during which the quality of the somatic cell can be preserved, to the collection date of the somatic cell to determine a latest delivery date on which the somatic cell is delivered to the cell production site latest, whereby a deliverable period between the earliest delivery date and the latest delivery date is calculated, and
determines the production period of the target cell based on an earliest producible period of the producible periods overlapping with the calculated deliverable period.

6. The cell production management system according to claim 1, wherein the second processor
adds a time of transportation of the somatic cell to the determined collection date of the somatic cell to determine the acceptance date of the somatic cell,
checks that the determined acceptance date is within the production period of the target cell, and
determines the acceptance date of the somatic cell.

7. The cell production management system according to claim 1, wherein the fourth processor
adds a time of transportation of the target cell to a completion date of the production period transmitted by the third medium to determine an earliest delivery date on which the target cell is delivered to a cell stock site earliest, and adds a quality assurance period during which the quality of the produced target cell can be ensured, to the completion date of the production period to determine a latest delivery date on which the target cell is delivered to the cell production site latest, whereby a deliverable period between the earliest delivery date and the latest delivery date is calculated, and
determines a stock period and a stock location where the target cell is stocked based on an earliest stockable period of the stockable periods overlapping with the calculated deliverable period.

8. The cell production management system according to claim 5, wherein the third processor adds a time of transportation of the target cell to a completion date of the determined production period to determine an earliest delivery date on which the target cell is delivered to a cell stock site earliest, and adds a quality assurance period during which the quality of the produced target cell can be ensured, to the completion date of the determined production period to determine a latest delivery date on which the target cell is delivered to the cell stock site latest, whereby a deliverable period between the earliest delivery date and the latest delivery date is calculated, and determines a stock period and a stock location where the target cell is stocked based on an earliest stockable period of the stockable periods overlapping with the calculated deliverable period, and subsequently subtracts the time of transportation of the target cell from a starting date of the determined stock period to determine a shipping date of the produced target cell, checks that the determined shipping date is after the completion date of the production period, and determines the shipping date of the target cell.

\* \* \* \* \*